United States Patent [19]

Loewy et al.

[11] Patent Number: 5,192,658
[45] Date of Patent: Mar. 9, 1993

[54] COMPOSITIONS AND PROTOCOLS APPLICABLE TO GENETIC ANALYSIS

[75] Inventors: Zvi G. Loewy, Bronx, N.Y.; Nancy Y. Ip, Stamford, Conn.; Howard J. Baum, Stony Point, N.Y.; Susan L. Leary, Hopewell Junction, N.Y.; Ingrid L. M. van de Stadt, Ossining, N.Y.

[73] Assignee: Lifecodes Corporation, Stamford, Conn.

[21] Appl. No.: 331,414

[22] Filed: Mar. 30, 1989

[51] Int. Cl.$^5$ .................. C12Q 1/68; C12Q 1/00; C07H 15/12
[52] U.S. Cl. ..................... 435/6; 435/974; 435/320.1; 536/27; 536/24.31; 935/78
[58] Field of Search ........... 536/27, 28, 24; 435/6, 435/252.3, 252.33, 230, 199; 935/97, 78, 79, 80, 27, 24, 6, 8

[56] References Cited

U.S. PATENT DOCUMENTS

| | | | |
|---|---|---|---|
| 4,720,454 | 1/1988 | White et al. | 435/6 |
| 4,785,086 | 11/1988 | Roshtchian et al. | 536/27 |
| 5,013,644 | 5/1991 | Severson et al. | 435/6 |
| 5,070,011 | 2/1991 | Parsons et al. | 435/6 |
| 5,077,400 | 12/1991 | Litt et al. | 536/27 |

OTHER PUBLICATIONS

Nicholls et al., *Cell*, vol. 49, 369–378 (1987).
Fischel-Ghodsian et al., *Nucleic Acids Research*, vol. 15, No. 15, 6197–6207 (1987).
Nicholls et al., *Nucleic Acids Research*, vol. 13, No. 21, 7569–7578 (1985).
Higgs et al., (*PNAS*), vol. 83, pp. 5165–5169 (1986).
Jeffreys et al., "Hypervariable 'Minisatellite' Regions in human DNA", *Nature* vol. 314 (1985).
Southern, D. M. (1975) "Detection of specific sequences among DNA fragments separated by gel electrophoresis," *J. Mol. Biol.* 98:503–517.
Jarman, A. P., R. D. Nicholls, D. M. Weatherall, J. B. Clegg and D. R. Higgs (1986) "Molecular characterisation of a hypervariable region downstream of the human alpha-globin gene cluster," *EMBO J.* 5:1857–1863.
Baird, M., K. Wexler, M. Clyne, E. Meade, L. Ratzlaff, G. Smalls, P. Benn, J. Glassberg, and I. Balazs (1987) "The application of DNA-print for the estimation of paternity," *Advances in Forensic Haemogenetics* 2:354–358 Springer-Verlag, New York; In Press.
Baird, M., A. Giusti, E. Meade, M. Clyne, R. Shaler, P. Benn, J. Glassberg, and I. Balazs (1987) "The application of DNA-PRINT TM for identification from forensic biological materials," *Advances in Forensic Haemogenetics* 2:396–402 Springer-Verlag, New York; In Press.
Baird, M., I. Balazs, A. Giusti, L. Miyazaki, L. Nicholas, K. Wexler, E. Kanter, J. Glassberg, F. Allen, P. Rubinstein, and L. Sussman (1986) Am. J. Hum. Genet. 39:489–501.

*Primary Examiner*—Margaret Moskowitz
*Assistant Examiner*—Bradley L. Sisson
*Attorney, Agent, or Firm*—Saliwanchik & Saliwanchik

[57] ABSTRACT

Polynucleotide sequences and other compositions useful for DNA polymorphism and other genetic analyses are disclosed herein. Also disclosed is a method for obtaining Variable Tandem Repeat polymorphism at a single genetic locus as well as other genetic analyses.

10 Claims, 15 Drawing Sheets

COMPOSITIONS AND PROTOCOLS APPLICABLE TO GENETIC ANALYSIS

DESCRIPTION

1. Field of the Invention

This invention relates to the field of molecular genetics. More specifically, this invention relates to polynucleotides useful for nucleic acid hybridizations, methods for producing these polynucleotides, and methods for applying these polynucleotides in genetic analysis.

2. Background of the Invention

Double stranded DNA is the most common form of depository of genetic information of organisms. Double stranded DNA has two complementary strands. Each strand is a polynucleotide sequence and the base sequences on the two complementary strands form Watson-crick base pairs. The duplex structure of DNA can be disrupted in a number of ways, for example, by heating a duplex DNA solution in a 0.1M NaCl to 100° C. for a few minutes. At this temperature, the two strands of duplex DNA separate. If the solution is gradually cooled, the two strands of duplex DNA can re-associate to reform the duplex structure.

The process of duplex formation from complementary polynucleotide or oligonucleotide sequences has been used advantageously for genetic analysis. Typically, a labeled polynucleotide or oligonucleotide sequence is used in a reassociation process whereby it forms a duplex structure with a substantially complementary sequence from a genetic source of interest. Because the labeled polynucleotide or oligonucleotide sequence is normally, though not necessarily, obtained from a source other than the source of interest, the process of association between complementary sequences has been known as nucleic acid hybridization, or just hybridization for short. The associational event provides genetic information about the source of interest through detection of the label on the labeled polynucleotide or oligonucleotide sequence. For this reason, the labeled polynucleotide or oligonucleotide sequence is called a probe. The label can be any suitable signal-generating moiety, and many such moieties are well known in the art.

Nucleic acid hybridization has been successfully applied in the study of DNA structure, gene purification, gene localization, the establishment of paternity and other familial relationship, genetic identity for forensic purposes, genetic identity of transplants, and detection and diagnosis of diseases and genetic traits.

One very powerful technique in the application of nucleic acid hybridization involves the fractionation of the complex genetic material to be analyzed prior to hybridization. E. M. Southern's procedure is the most widely used. See Southern, J. Mol. Bio. 98: 503-517 (1975). Such a genetic analysis can reveal not only the presence or absence of complementary target nucleic acid sequences, but also the size of the restriction fragment(s) containing the target sequence. Genetic variations within a species may be reflected by variations among individuals in the size of the restriction fragments containing a particular target sequence. Conversely, genetic relatedness of a group of individuals may be reflected by a deviation from random variations that exist among unrelated individuals. This aspect of genetic analysis has been called Restriction Fragment Length Polymorphism (RFLP).

The genetic information which can be adduced using "single-copy" DNA probes depends on the number of probes used, the number of genetic loci each probe is capable of detecting, the heterozygosities and the allele frequency of the relevant genetic loci. To date, "single-copy" DNA sequences are known to detect only a single locus per sequence. Moreover, heterozygosity of DNA in higher organism is low. In man, it is about 0.001 per base pair. Finally, most polymorphic states detected are only dimorphic (i.e. there are only two representational states: absence or presence of a relevant restriction site on the restriction fragment in question). As is often the case, critical individuals in a genetic analysis are homozygous, and the genetic analysis may be uninformative.

Genetic analysis in higher organisms has been simplified considerably by the availability of probes for hypervariable regions of genomic DNA. These hypervariable regions show multi-allelic variation and high heterozygosities. These regions also appear to be widely interspersed within the genome. In each case, the hypervariable region comprises a variable number of tandem repeats of a short sequence (thus, Variable Tandem Repeats or VTR), and polymorphism results from allelic differences in the number of repeats at a given locus. This type of polymorphism, a subclass of RFLP has been called VTR Polymorphism. It is believed that the variation in repeat number arises by mitotic or meiotic unequal exchanges or by DNA "slippage" during replication. Therefore, if genomic DNA is digested with a restriction endonuclease which does not cut within the repeat unit, and if a genetic locus encompasses a variable tandem repeat or VTR, allelic markers would exist for that locus. (It should be noted that the so-called repeat unit is a hypothetical consensus sequence, and any actual VTR sequence in the genome is really a string of short "core" sequences, each of which is very highly homologous, but usually not identical to the consensus sequence. Indeed, a "core" sequence may differ in length from the consensus sequence. The consensus sequence is derived from examining and "averaging" over a large number of "core" sequences. A "core" sequence is typically at least 70%, but often more than 70%, homologous to the consensus sequence.)

Jarman et al. have described a hypervariable region of DNA located 8-kb downstream of the human alpha globin complex (EMBO J.5: 1857-63 [1986]). This hypervariable region is composed of an array of imperfect 17-bp tandem repeats, the number of which differs considerably (70-450) from one allele to another. Thus, this locus is highly polymorphic. Genetic polymorphism which reflects variations in the number of such tandem repeats among individuals has been called Variable Tandem Repeat Length Polymorphism.

The VTR described by Jarman et al., supra, cross-hybridizes with other hypervariable genetic loci at low stringency. Thus a polynucleotide probe prepared from this region is potentially a very powerful probe, capable of probing many genetic loci in a single try.

A typical RFLP analysis involves digesting target genomic DNA with a restriction endonuclease, separating the digested DNA by gel electrophoresis, transferring the fractionated DNA in a denatured state to a binding surface, hybridizing the transferred DNA with a suitable probe, detecting the signals generated by the probe molecules which have become hybridized to the target DNA. The pattern of the signals generated would provide information about the target DNA. The pattern of signals can also be stored for later use, for instance, to determine or confirm an individual's identification (i.e., the pattern would be the individual's genetic fingerprint).

More commonly, two or more target DNAs are processed for RFLP analysis. Depending on the sources of the target DNA, the information generated by comparison of the patterns can be used immediately as in the case of genetic identity (e.g., identification of a suspect of a crime), or in the case where a high degree of genetic relatedness is present (e.g., paternity testing, sib analysis and the like). In other cases, the information derived from pattern comparison may form a part of a larger information-gathering effort. Pedigree analysis of distant relatives and correlation of a gene of genotype with a trait or medical condition are but two examples.

However the RFLP analysis is to be used, the pattern of signals is controlled in large part by the probe or probes used in the analysis. A polynucleotide probe may be useful for any of a number of features.

First, a probe may be able to detect polymorphism at a locus that other probes cannot detect. The locus may be particularly useful for genetic analysis in the general population because it has many evenly distributed alleles. Alternatively, the locus may be particularly useful for genetic analysis in a highly restricted segment of the population because it has a rare allele.

Second, a probe may be able to detect many loci simultaneously and unambiguously when a particular restriction endonuclease is used to digest the target DNA. In this connection, it is useful to note that certain restriction endonucleases may be preferred because of the history of the target DNA samples, e.g. forensic samples which has been exposed to the elements for an extended period of time.

Third, probes are often used in combination simultaneously because their resolving power may be compounded. Compounding is obtained when the signals produced by the several probes do not overlap and permit unambiguous assignment of each (or substantially each) signal to an allele of a locus. See, e.g., "The Application Of DNA-Print For The Estimation Of Paternity", Baird et al. in Advances in Forensic Haemogenetics 2: 354–358, Springer-Verlag, New York (1987).

How RFLP phenotypes can be practically applied for paternity and forensic determinations have been discussed in Baird et al., supra; Baird et al. (II), "The Application Of DNA-Print ™ For Identification From Forensic Biological Materials", in Adv. in Forensic Haemogenetics 2: 396–402, Springer-Verlag, New York (1987); and Baird et al. (III), Am. J. Hum. Genet. 39:489–501 (1986) and citations therein. These papers are hereby incorporated by reference.

For the purpose of this invention, a "discrete polynucleotide sequence or subsequence" means a polynucleotide sequence or subsequence of greater than 15 nucleotides, but preferably greater than 50 nucleotides, and very preferably greater than 100 nucleotides; and a polynucleotide means a chain of about 15 nucleotides or more, and embraces the upper range of what sometimes passes as oligonucleotides.

BRIEF SUMMARY OF THE INVENTION

The subject invention concerns the following:

(1) polynucleotide sequences useful for detecting polymorphism in a species of organism of interest, or a subpopulation thereof;

(2) a polynucleotide sequence useful for detecting polymorphism at a single genetic locus, and characterized by its ability to form hybrids with restriction fragments of DNA, of 5.9 and 4.6 kilobases, produced by PstI digestion of genomic DNA extracted from K562 cells;

(3) a polynucleotide sequence useful for detecting polymorphism at a single genetic locus and capable of forming hybrids with genomic DNA fragments produced by complete digestion of Caucasoid, American Black, Hispanic, or Oriental genomic DNA with the restriction endonuclease PstI of approximate allelic lengths and allelic frequencies as given in Table 1;

(4) the use of the above-described polynucleotide sequence as a probe for polymorphism;

(5) a method of genetic analysis comprising:
  (a) digesting a DNA sample with a restriction endonuclease;
  (b) separating the DNA restriction fragments according to size by electrophoresis;
  (c) transferring the separated DNA to a binding surface;
  (d) hybridizing the transferred DNA with a polynucleotide probe labeled with a signal-generating moiety, wherein the polynucleotide probe is a polynucleotide probe of the present invention; and
  (e) detecting the signal generated; whereby the pattern of signals generated provides information about the composition of the DNA sample; and (6) recombinant vectors and cells useful for producing polynucleotides of the invention.

BRIEF DESCRIPTION OF THE DRAWINGS

FIG. 5b shows as hybridization blot of PstI digested genomic DNA probed with pAC404 for the individuals diagrammed in FIG. 5a.

DETAILED DESCRIPTION OF THE INVENTION

Figure 1:
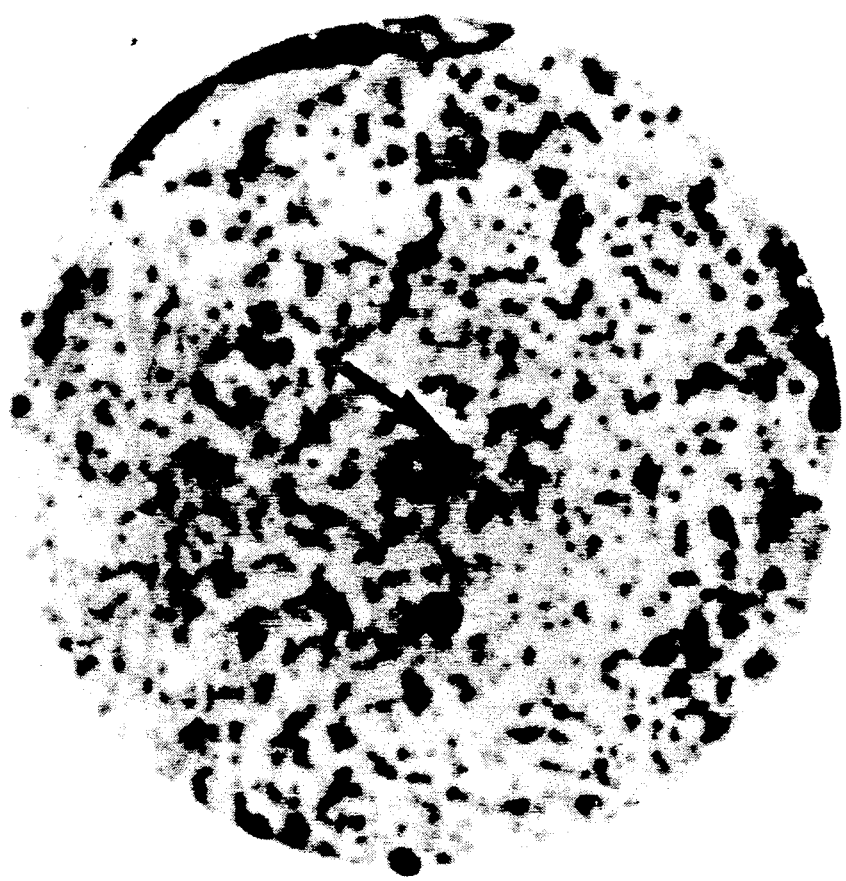
FIG. 1 shows an autoradiogram of the plaque hybridization with the synthetic probe derived from the 17-base consensus sequence of the VTR at the 3' end of the human alpha globin complex. Phase Lila 4 is identified by the closed arrow.

One embodiment of the instant invention is a method to obtain polynucleotide sequences useful for detecting polymorphism in a species, or a subpopulation thereof. A library of genomic DNA digested with one or more restriction endonucleases and cloned in a suitable recombinant vector is screened with a polynucleotide probe which comprises a string of "core" sequences (hereinafter "screening probe"). This string of "core" sequences can, but need not be, a monomer, an oligomer or a polymer or a mixture of oligomers and polymers of a consensus sequence or "core" sequence of a VTR. Preferably, the screening probe is a mixture of oligomers of a consensus sequence, because a short consensus sequence can be easily synthesized chemically in large amounts and ligated to form a mixture of oligomers. In a preferred embodiment, the consensus sequence is 5'-CCCCCCGTGTCGCTGTT-3'.

For the purpose of generating a genomic library, it is preferred that the restriction endonuclease digestion of genomic DNA be incomplete. One reason is that many genomic VTR sequences may otherwise evade detection. This would be so if the relevant restriction endonuclease cuts within the VTR sequences, and the bulk of the VTR sequences will be in relatively small pieces. The smaller the pieces, the greater the number of recombinant molecules which must be studied so that the human genome will be covered. For the same reason, it is preferred that a recombinant vector which can accommodate a large DNA insert be used. Finally, where the recombinant vector has a restricted cloning range, incomplete digestion of the genomic DNA would also tend to avoid under-representation in the library of completely digested products which are smaller than the preferred cloning sizes.

The recombinants which react positively with the screening probe in a hybridization test (hereinafter "positive recombinants") are selected for further examination. In a preferred embodiment, the recombinants are bacteriophages. The standard method of "phage lifts" can be used to identify the recombinants containing DNA inserts which hybridizes to the probe. See Maniatis et al., *Molecular Cloning: A Laboratory Manual*, Cold Spring Harbor Laboratories, Cold Spring Harbor, N.Y., (1982). Briefly, a portion of a phage plaque is transferred to a nylon membrane where the DNA of the phage is immobilized and probed. Many plaques can be transferred in a single lift; moreover, the position of a plaque on the growth plate is in a one-to-one correspondence with the position on the membrane, thus permitting identification of the plaques which give rise to positive results in a hybridization test with the probe. Obviously, many variations of this basic technique can be designed with other cloning and/or transfer and/or identification systems.

Once the positive recombinants have been identified, they can be subjected to tests which prove or disprove their utility. They are used as probes in hybridization tests against genomic sequences of a species of organism of interest, or a relevant subpopulation thereof. While the present invention broadly encompass eukaryotic organisms, one of the more commercially significant use is that of probing mammalian genomes, particularly, the human genome. In any case, it is very highly preferred that the probe sequences of the present invention be derived from the same species of organisms as the genetic materials which are to be tested in a hybridization test. Thus, for applications of human genetic analysis, the starting library should preferably be a human genomic library. To avoid verbosity, the embodiments of this invention are described as if they apply to humans specifically. The present invention is not so limited, and is to be construed to be applicable generally to mammals and other eukaryotes.

The useful positive recombinants are those which can detect polymorphism in humans, at a single locus, and under high stringency conditions. Genomic DNAs from related individuals are separately digested with a restriction endonuclease, the digests are separately subjected to size fractionation by, for example, electrophoresis, and the fractionated restriction fragments are prepared for hybridization in any standard method. Positive recombinants or the human sequences or discrete polynucleotide subsequences inserted therein (jointly and severally "test sequences") are used to probe the restriction digests. Preferably, a single test sequence is used at a time. However, several sequences can be grouped together in preliminary tests to determine whether the group as a whole contains any useful sequences.

The hybridization "banding" pattern for each individual member is determined. In particular, the sizes of restriction fragments which hybridize to the test sequences are determined. The segregation scheme of each band within a family or, more commonly, a number of families will inform as to the nature of the genetic locus (loci) being detected. The nature of a genetic locus includes, but is not limited to, the following: 1) Mendelian or non-Mendelian segregation; 2) phenotype and frequency of alleles (reflected by the size of restriction fragments produced by the restriction endonuclease used to digest the genomic DNA, and the frequency of occurrence in a population). If the test sequence detects bands of a locus that represent different-sized fragments among different individuals, it is capable of detecting polymorphism in that polymorphic locus. The determination of the nature of the locus (loci) detected by a test sequence from the segregation scheme is a straight forward application of classical genetics, and is well within the command of a person of ordinary skill in the art of molecular genetics. The size of families, and the number of families needed to provide sufficient information to work out the segregation scheme would vary with the number of genetic loci being detected by the test sequence, the number of alleles in these loci, and the frequency of each allele. An ordinarily skilled artisan would also know how to determine the number and size of families to be studied.

Another embodiment of the instant invention is the test sequences which can detect polymorphism in a species of organism of interest, or a subpopulation thereof (hereinafter "useful test sequence").

In another embodiment of the instant invention, useful test sequences are cloned in recombinant vectors. In another embodiment, the recombinant vectors comprising the useful test sequences are harbored in a cell. Molecular cloning and transformation methods are well known in the art.

Because the segregation scheme is both lengthy and expensive to workout, it is sometimes preferable to defer the study of segregation until a test sequence has been better characterized. Thus, it may be preferable to modify the method described hereinabove, namely, to use instead of genomic DNAs from members of families, merely genomic DNAs from random, unrelated individuals. If the banding pattern appear to vary from individual to individual, the test sequence is presumptively treated as being useful as a polymorphic probe.

The presumptively useful test sequence is analyzed, and less desirable sequence(s) are removed to produce an improved test sequence. For example, a test sequence may comprise a subsequence which is polymorphic as well as a subsequence which is non-polymorphic in the relevant population. The presence of non-polymorphic bands yields no useful genetic information about a human individual, but can interfere with genetic analysis by, for example, obscuring a partially or totally informational band detected by a second probe used in combination with the test sequence. Another example is where the test sequence comprises a subsequence which is a highly repetitive sequence in the human genome. An example of a highly repetitive sequence is the "Alu sequence". See Houck et al., J. Mol. Biol. 132: 289-306 (1979). Presence of such highly repetitive sequences in a probe often cause a high non-informational background signal in a hybridization blot. This background signal can be avoided by eliminating the highly repetitive sequence component from the test sequence. See, for example, Sealey et al., Nuc. Acids Res., 13: 1905-1922 (1985).

Still another example is where the test sequence comprise a first subsequence which delivers only a small signal in a hybridization blot relative to the signal delivered by a second subsequence. Here, it may be more advantageous to eliminate the first test subsequence so that a more "cost-effective" probe which delivers a higher signal on a per nucleotide basis may be produced. A more specific example of this type is where the first subsequence is a "single-copy" sequence, and the second subsequence is a Variable Tandem Repeat Sequence. On a per nucleotide basis, the second sequence delivers more signal whenever there are more than a single copy at a genetic locus.

Discrete polynucleotide subsequences may be obtained from a test sequence in a number of ways, and are well within the capability of an ordinarily skilled artisan. For example, one end of the test sequence may be progressively removed by an exonuclease or S1 enzyme, while the other end is being protected. Another example is digestion with a restriction enzyme. Other methods of obtaining subsequences are within the contemplation of the present invention.

After the less desirable subsequences have been eliminated from a test sequence, the remaining portion of the test sequence is used in familial tests for the determination of the nature of the genetic locus (loci) which it is capable of detecting as described above.

Finally, nearby genomic sequences (including nearby VTR sequences) may be reached by chromosome walk.

As discussed in the Background section of this application, duplex formation and stability depend on substantial complementarity between the two strands of a hybrid, and a certain degree of mismatch can be tolerated. Therefore, whenever a test sequence obtained as described hereinabove has been determined to be useful in probing target polynucleotides of interest, mutations (both single and multiple), deletions, insertions of the useful test sequence, and combinations thereof, wherein said mutations, insertions and deletions permit formation of stable hybrids with said target polynucleotide of interest, are part of the present invention. Mutations, insertions and deletions can be produced in a given polynucleotide sequence in many ways, and these methods are known to an ordinarily skilled artisan. Other methods may become known in the future. The known methods include, but are not limited to: 1. determining analytically the sequence of a test sequence of the present invention, synthesize chemically or otherwise an artificial sequence which is a mutation, insertion or deletion of the test sequence; 2. using a test sequence of the present invention to obtain via hybridization a genomic sequence or otherwise which is a mutation, insertion or deletion of the test sequence; and 3. mutating, inserting or deleting a test sequence in vitro or in vivo.

It is important to note that the mutational, insertional, and deletional variants generated from a given test sequence may be more or less efficient than the test sequences, in the sense that (a) more or fewer genetic loci may become detectable, (b) more or fewer alleles of a particular locus may become detectable, (c) more or less stable under stringent hybridization conditions, and (d) any combination of the above. Notwithstanding such differences in efficiency, these variants are within the scope of the present invention.

In another embodiment of the present invention, the useful test sequences described hereinabove are used for genetic analysis, (i.e., used as probes), including but not limited to analysis of genetic identity, relatedness or alteration. In one preferred embodiment, the method of genetic analysis comprises:

(a) digesting a DNA sample with a restriction endonuclease;

(b) separating the DNA restriction fragments according to size by electrophoresis;

(c) transferring the separated DNA in a state suitable for hybridization to a binding surface;

(d) hybridizing the transferred DNA with a useful test sequence labeled with a signal-generating moiety, and (e) detecting the signals generated;

whereby the pattern of signals generated provides information about the composition of the DNA sample.

This and other embodiments of the present invention involve the use of useful test sequences as probes in methods of genetic analysis.

EXAMPLES

Following are examples which illustrate procedures, including the best mode, for practicing the invention. These examples should not be construed as limiting. All percentages are by weight and all solvent mixture proportions are by volume unless otherwise noted.

Example 1—Detection of Genomic Sequences which Hybridize with Oligomers of a Consensus Sequence of a VTR Human genomic DNA incompletely digested with the restriction endonuclease EcoRI was cloned into the bacteriophage lambda Charon 30. Restriction fragments ranging from 4.5 kbp to 17.5 kbp can be cloned into this vector. [Gene 12: 301-309 (1980)]. About 5000 phage plaques were screened according to the method of Maniatis et al., supra, at page 321. Oligomers of 5'-CCCCCCGTGTCGCTGTT-3', the 17-base consensus sequence of VTR at the 3' end of the human alpha globin complex, with an average length of 200-300 bases, were used to screen the phage "lifts". FIG. 1 shows the result of the plaque hybridization. The arrow identifies the phage Lila 4 which is further characterized in subsequent examples.

Example 2—Analysis of Human Sequences in the Recombinant Phage, Lila 4

Figure 2:
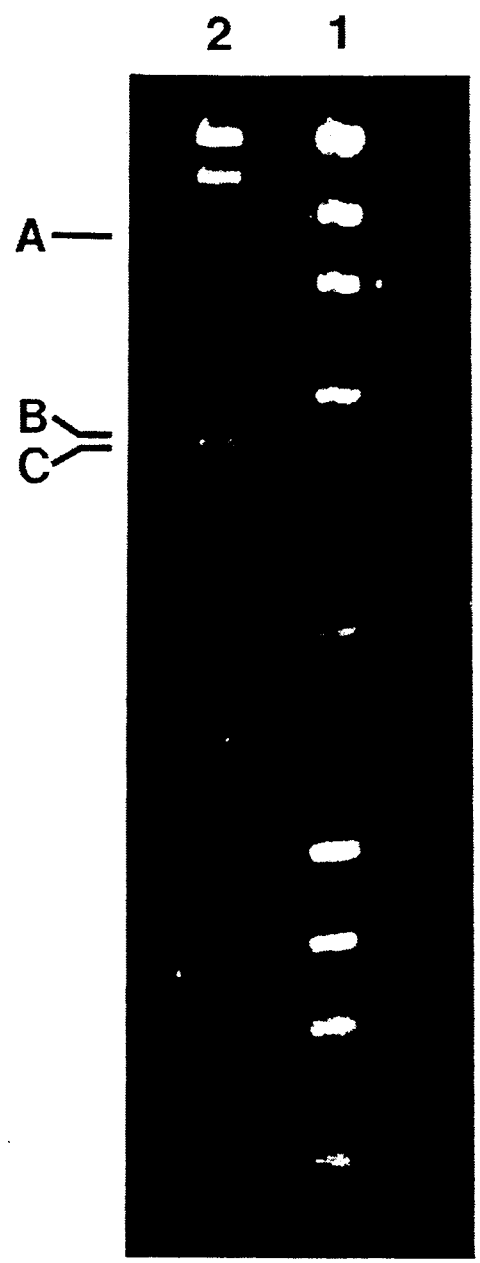
FIG. 2 shows the electrophoretic pattern of restriction fragments of DNAs from the recombinant lambda phage Lila 4 which was digested with EcoRI. Lane 1 corresponds to Hind III digested lambda and Hae III digested Phi-x 174 markers. The Lila 4 EcoRI digest is shown in lane 2. Three human genomic inserts are identified as Band A, Band B, and Band C.
Figure 3A:
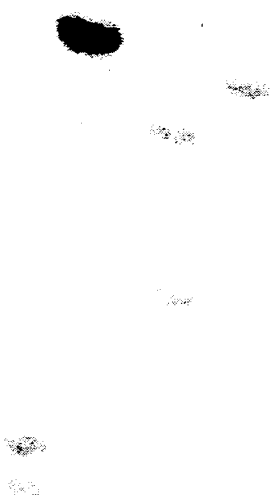
FIG. 3a shows a Southern blot of Pst I digested human genomic DNA from four unrelated individuals (lanes 1–4) probed with pAC387. The pAC387 corresponds to the 8 kb EcoRI fragment probe (Band a-FIG. 2).
Figure 3B:
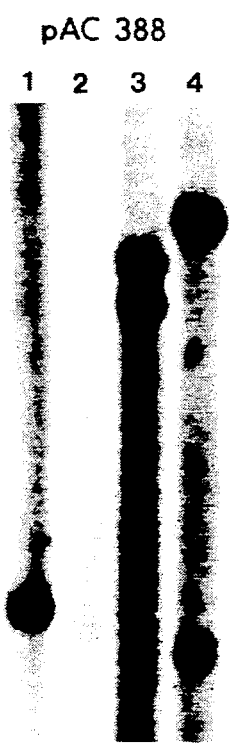
FIG. 3b shows a Southern blot of Pst I digested human genomic DNA from four unrelated individuals (lanes 1–4) probed with pAC388. The pAC388 corresponds to the 3 kb RsaI fragment probe.
Figure 3C:
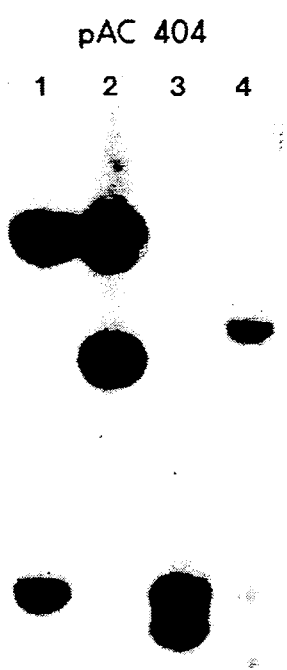
FIG. 3c shows a Southern blot of PstI digested human genomic DNA from four unrelated individuals (lanes 1–4) probed with pAC404. The pAC404 corresponds to the 1.6 kb HacIII fragment probe.
Figure 3D:
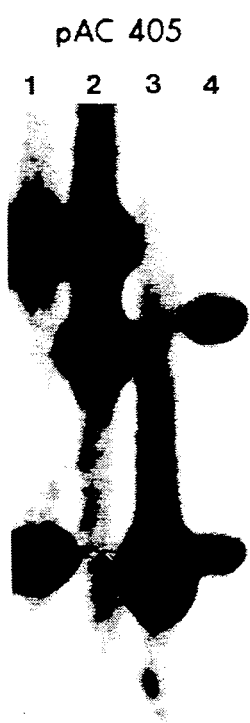
FIG. 3d shows a Southern blot of PstI digested human genomic DNA from four unrelated individuals (lanes 1–4) probed with pAC405. The pAC405 corresponds to the 0.3 kb HacIII fragment probe.

DNA from Phage Lila 4 was extracted and digested with the restriction endonuclease EcoRI. The digests were subjected to electrophoresis in an agarose gel. The electrophoretic pattern obtained is shown in FIG. 2. Lane 1 contained bacteriophages lambda HindIII fragments and Phi-x 174 Hae III fragments as molecular weight markers. The top two bands in Lane 2 correspond to the arms of the cloning phage vector. Bands A, B, & C are human genomic sequence inserts. Band A is approximately 8 Kb in size and Bands B and C are approximately 4 Kb in size.

Example 3—Human Genomic Sequence Inserts from Phage Lila 4 as Polymorphic Probes To characterize the human genomic inserts in Phage Lila 4 DNAs corresponding to Bands A, B, and C of FIG. 2 were isolated. They were used independently in the Southern format to probe human genomic DNAs from related individuals. Target human sequences were restricted with PstI.

In the experiment shown in FIG. 3, 5 ug of PstI digested DNA from each individual was electrophoresed and blotted onto a nylon membrane. The probe, pAC387 insert, corresponded to [alpha-P$^{32}$]-labeled DNA from Band A of FIG. 2. Radioactive labeling was achieved by random 6-mer primed enzymatic synthesis, using radioactive precursors as substrates. However, other methods of labeling would also work as well. Total unlabeled human genomic DNA was added as a precautionary measure to the 8 Kb probe. It was known that the human genome contains widely dispersed highly repetitive sequences such as the Alu sequences. If the human insert in Phage Lila 4 contained these and/or similar highly repetitive sequences, such repetitive sequences would produce a heavy background signal over the entire area on the blot where human target DNA could be found. The introduction of total human genomic DNA would serve to suppress this background signal. Sealey et al., supra.

All hybridizations were carried out at 65° C. in 5X SSPE, 1-2% SDS (sodium dodecylsulfate), 0.5-1 mg/ml heparin. The blots were washed in 0.1X SSC, 2.5 mM sodium phosphate, 1% SDS at 65° C., [1X SSPE=0.16M NaCl, 0.01M sodium phosphate, and 1 mM ethylenediaminetetraacetic acid. 1XSSC=0.15M NaCl, 0.015M sodium citrate]. The blots were exposed at −70° C. Analysis of the autoradiograms revealed a polymorphic pattern with an allele distribution of 4-7 Kb with the 8 Kb fragment probe (Band A in FIG. 2). The two remaining human sequences, (Band B and Band C in FIG. 2) failed to result in a polymorphic pattern. Consequently, the 8 Kb fragment was isolated and further characterized.

Example 4—Cloning of the Human "Polymorphic Probe" Sequence from Phage Lila 4

Figure 4:
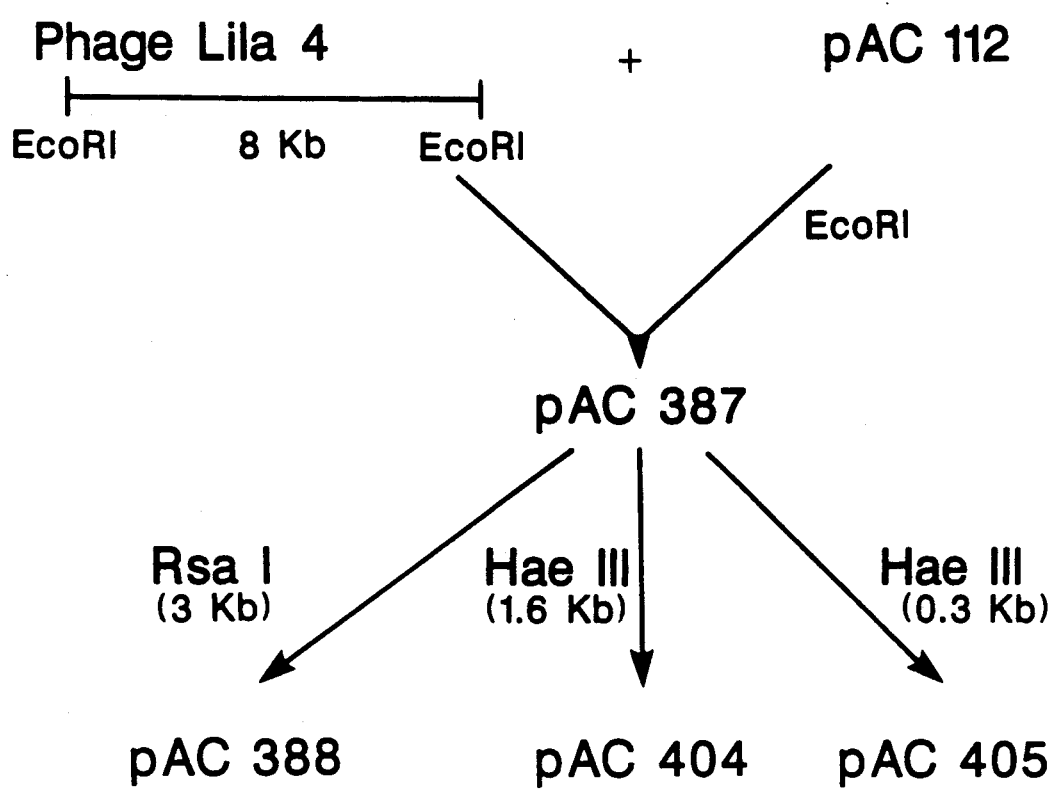
FIG. 4 is a schematic representation of the plasmid subclones of phage Lila 4. pAC387 contains the 8 Kb insert from the phage. pAC388, pAC404, and pAC405 are all derived from the insert in pAC387.

The 8 Kb fragment, corresponding to Band A in FIG. 2, was isolated and inserted into pAC112 (Bluescribe, Strategene Inc.) that was restricted with EcoRI. The resulting construct was identified as pAC387 (FIG. 4). The human sequence insert in pAC387 was further subcloned by isolating the 8 Kb insert and digesting it with either RsaI or HaeIII. One RsaI fragment corresponding to a size of 3 Kb generated a polymorphic pattern on Pst I blots (FIG. 3, Panel pAC388). This 3 Kb fragment was isolated and ligated into pAC262 (Bluescript, Strategene Inc.) that was restricted with EcoRV, resulting in pAC388. A third recombinant of the Lila 4 probe was obtained by isolating a 1.6 Kb Hae III fragment which produced a polymorphic pattern on Pst I blots (FIG. 3, Panel pAC404) and inserting this fragment into pAC262 that was restricted with SmaI. This plasmid was identified as pAC404. A fourth recombinant of the Lila 4 probe was generated by ligating the 1.6 Kb Hae III fragment with pAC262 that was digested with SmaI. This plasmid was termed pAC405 (FIG. 4). The human sequence insert size in pAC405 is approximately 0.3 Kb. Apparently, sequences from the 1.6 Kb fragment were deleted during the ligation transformation. Interestingly, the insert from pAC405 produces a strong signal on Pst I blots (FIG. 3, panel pAC405). A schematic representation of the four plasmid subclones of Lila 4 is shown in FIG. 4.

Figure 5A:
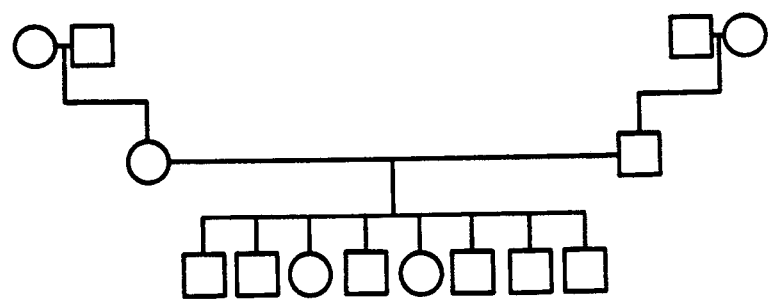
FIG. 5a shows a family lineage diagram covering three generations.
Figure 5B:
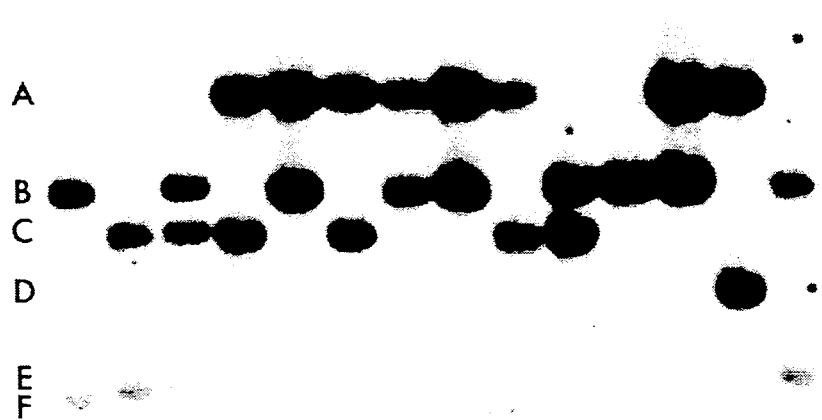
Figure 6A:
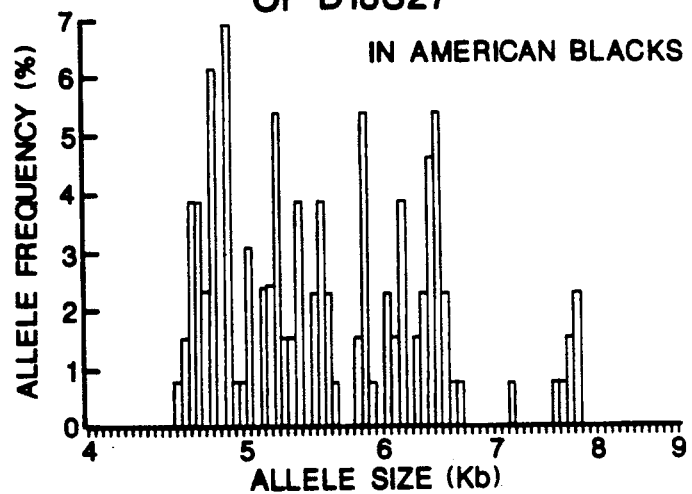
FIG. 6 shows the allelic distributions of the genetic locus detectable by pAC404 in American Blacks (FIG. 6A), Caucasoids (FIG. 6B), Chinese Orientals (FIG. 6C), and Hispanics (FIG. 6D).
Figure 6B:
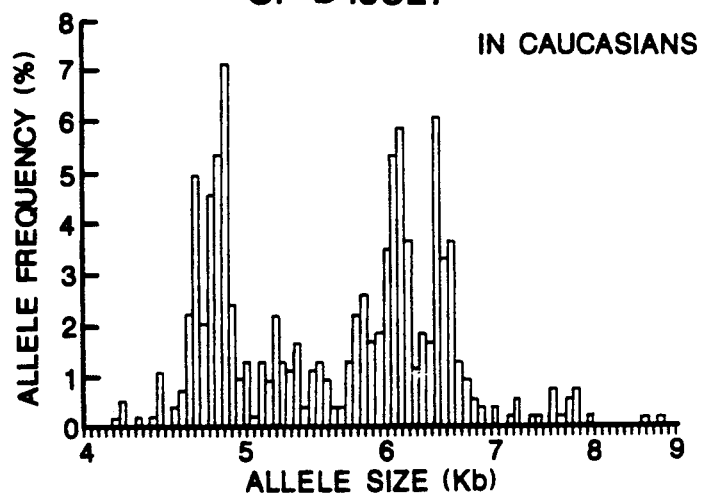
Figure 6C:
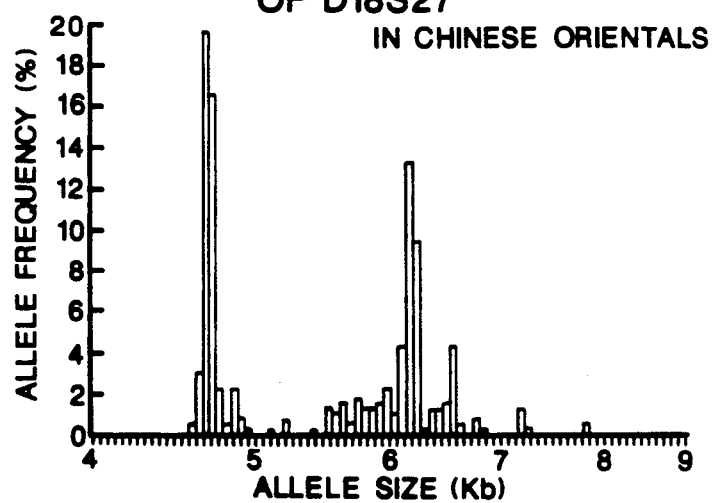
Figure 6D:
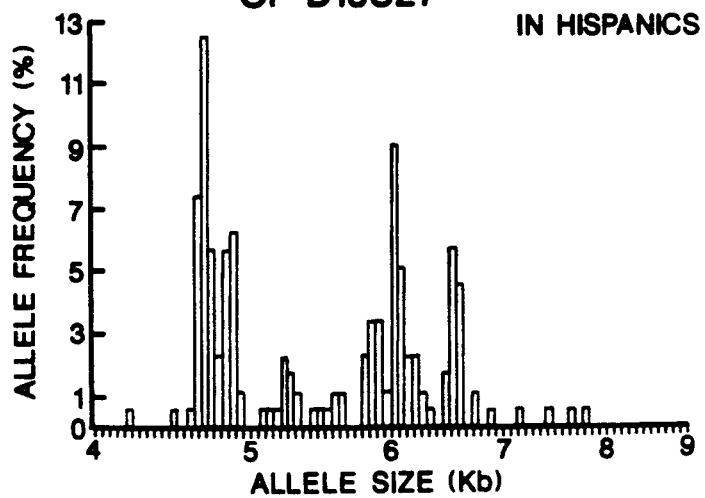

Example 5—pAC404 Detects Single Locus which Segregate Independently in the Mendelian Fashion Genomic DNAs were extracted from individuals belonging to families spanning three generations digested with Pst I, and probed with the pAC404 insert in the Southern format. FIG. 5 shows the results of one such family study. The family tree at the top of the figure indicates the source of DNA in each of the test lanes.

A total of 6 bands of varying sizes were detected by hybridization with pAC404. These are identified on the side of the figure.

Several conclusions can be drawn from these results. First, each and every band which is present in any one of the eight children is also present in either the father or the mother. This result is consistent with stable chromosomal inheritance. Similarly, every band which is present in the parents is present in their respective parents.

Second, the results are consistent with independent Mendelian segregation of alleles present on sister chromosomes. For example, Bands B and C appear to be two alleles to the same gene. The mother has both of these alleles, presumably one on each sister chromosome. However, each of the eight children inherits one of the other allele, but never both. Thus, the mode of inheritance is consistent with independent Mendelian segregation. Similarly, bands A and B in the father segregate in a manner which is consistent with the notion that they are two alleles on the same gene.

Example 6—Population Genetics and Allele Frequency

DNA from 615 genetically unrelated individuals were tested in this study. Each DNA sample was digested with Pst I and probed with pAC404 in a Southern hybridization procedure. The results were sorted according to their ethnic origins (i.e., American Blacks, Caucasoids, Hispanics, and Chinese Orientals). The frequency vs. allele size distributions are shown in FIG. 6. D18527 is the assignment number designated by the Human Gene Mapping Library. FIGS. 6A, 6B, 6C and 6D show the distributions in American Blacks, Caucasoids, Chinese Orientals, and Hispanics, respectively. The Y-axis is measured in percent, and the X-axis is measured in kilobase pairs. The frequency distributions are more fully set forth in Table 1.

TABLE 1

Allele Frequencies For Four Racial Groups**
Fragment Size (kilobases)***

| | 4.16 | 4.20 | 4.25 | 4.29 | 4.33 | 4.37 | 4.42 | 4.46 | 4.51 |
|---|---|---|---|---|---|---|---|---|---|
| Blacks | 0 | 0 | 0 | 0 | 0 | 0 | 0 | 0 | 0.8 |
| Caucasoids | 0.2 | 0.6 | 0 | 0.2 | 0 | 0.2 | 1.1 | 0 | 0.4 |
| Hispanics | 0 | 0.6 | 0 | 0 | 0 | 0 | 0 | 0.6 | 0 |
| Chinese Orientals | 0 | 0 | 0 | 0 | 0 | 0 | 0 | 0 | 0 |

| | 4.55 | 4.60 | 4.64 | 4.69 | 4.74 | 4.78 | 4.83 | 4.88 | 4.93 |
|---|---|---|---|---|---|---|---|---|---|
| Blacks | 1.5 | 3.9 | 3.9 | 2.3 | 6.2 | 4.6 | 6.9 | 0.8 | 0.8 |
| Caucasoids | 0.7 | 2.2 | 5.0 | 2.0 | 4.6 | 5.3 | 7.1 | 2.4 | 0.9 |
| Hispanics | 0.6 | 7.4 | 12.5 | 5.7 | 2.3 | 5.7 | 6.3 | 1.1 | 0 |
| Chinese Orientals | 0.5 | 3.1 | 20.0 | 16.6 | 2.3 | 0.5 | 2.3 | 0.8 | 0.3 |

| | 4.98 | 5.03 | 5.08 | 5.13 | 5.18 | 5.23 | 5.29 | 5.34 | 5.39 |
|---|---|---|---|---|---|---|---|---|---|
| Blacks | 3.1 | 0 | 2.3 | 2.3 | 5.4 | 1.5 | 1.5 | 3.9 | 0 |
| Caucasoids | 1.3 | 0.2 | 1.3 | 0.9 | 2.2 | 1.3 | 1.1 | 1.7 | 0.4 |
| Hispanics | 0 | 0.6 | 0.6 | 0.6 | 2.3 | 1.7 | 1.1 | 0 | 0.6 |
| Chinese Orientals | 0 | 0 | 0.3 | 0 | 0.8 | 0 | 0 | 0 | 0.3 |

| | 5.45 | 5.50 | 5.55 | 5.61 | 5.67 | 5.72 | 5.78 | 5.84 | 5.90 |
|---|---|---|---|---|---|---|---|---|---|
| Blacks | 2.3 | 3.9 | 2.3 | 0.8 | 0 | 0 | 1.5 | 5.4 | 0.8 |
| Caucasoids | 1.1 | 1.3 | 0.9 | 0.4 | 0.4 | 1.3 | 2.2 | 2.6 | 1.7 |
| Hispanics | 0.6 | 0.6 | 1.1 | 1.1 | 0 | 0 | 2.3 | 3.4 | 3.4 |
| Chinese Orientals | 0 | 1.3 | 1.0 | 1.5 | 0.5 | 1.8 | 1.3 | 1.3 | 1.5 |

| | 5.96 | 6.02 | 6.08 | 6.14 | 6.20 | 6.26 | 6.32 | 6.39 | 6.45 |
|---|---|---|---|---|---|---|---|---|---|
| Blacks | 0 | 2.3 | 1.5 | 3.9 | 0 | 1.5 | 2.3 | 4.6 | 5.4 |
| Caucasoids | 1.8 | 3.5 | 5.3 | 5.9 | 3.7 | 1.1 | 1.8 | 1.7 | 6.0 |
| Hispanics | 1.1 | 9.1 | 5.1 | 2.3 | 2.3 | 1.1 | 0.6 | 0 | 1.7 |
| Chinese Orientals | 2.3 | 1.0 | 4.3 | 13.3 | 9.4 | 0.3 | 1.3 | 1.3 | 1.5 |

| | 6.51 | 6.58 | 6.64 | 6.71 | 6.78 | 6.85 | 6.91 | 6.98 | 7.05 |
|---|---|---|---|---|---|---|---|---|---|
| Blacks | 2.3 | 0.8 | 0.8 | 0 | 0 | 0 | 0 | 0 | 0 |
| Caucasoids | 3.3 | 3.7 | 1.3 | 0.9 | 0.6 | 0.4 | 0 | 0.4 | 0 |
| Hispanics | 5.7 | 4.6 | 0 | 1.1 | 0 | 0.6 | 0 | 0 | 0 |
| Chinese Orientals | 4.3 | 0.5 | 0 | 0.8 | 0.3 | 0 | 0 | 0 | 0 |

TABLE 1-continued

| | 7.12 | 7.19 | 7.27 | 7.34 | 7.41 | 7.49 | 7.56 | 7.64 | 7.71 |
|---|---|---|---|---|---|---|---|---|---|
| Blacks | 0.8 | 0 | 0 | 0 | 0 | 0 | 0.8 | 0.8 | 1.5 |
| Caucasoids | 0.2 | 0.6 | 0 | 0.2 | 0.2 | 0.2 | 0.7 | 0.2 | 0.6 |
| Hispanics | 0.6 | 0 | 0 | 0 | 0.6 | 0 | 0 | 0.6 | 0 |
| Chinese Orientals | 1.3 | 0.3 | 0 | 0 | 0 | 0 | 0 | 0 | 0 |

| | 7.79 | 7.87 | 7.95 | 8.03 | 8.11 | 8.19 | 8.27 | 8.35 | 8.44 |
|---|---|---|---|---|---|---|---|---|---|
| Blacks | 2.3 | 0 | 0 | 0 | 0 | 0 | 0 | 0 | 0 |
| Caucasoids | 0.7 | 0 | 0.2 | 0 | 0 | 0 | 0 | 0 | 0 |
| Hispanics | 0.6 | 0 | 0 | 0 | 0 | 0 | 0 | 0 | 0 |
| Chinese Orientals | 0.5 | 0 | 0 | 0 | 0 | 0 | 0 | 0 | 0 |

| | 8.52 | 8.61 | 8.69 | 8.78 |
|---|---|---|---|---|
| Blacks | 0 | 0 | 0 | 0 |
| Caucasoids | 0 | 0.2 | 0 | 0.2 |
| Hispanics | 0 | 0 | 0 | 0 |
| Chinese Orientals | 0 | 0 | 0 | 0 |

**Allele frequencies are stated in percent in Table 1.
***The standard error for fragment size is approximately 0.6% of the size of the fragment. Therefore, DNA fragments whose sizes are within 2% of each other (3 standard deviations) are considered indistinguishable.

Example 7—Characterization of pAC404

Genomic DNA from various human cell lines were extracted, digested with PstI, and hybridized with pAC404 insert in the Southern format. 7024, 7351, 7047, 7432, 7433 and 7015 were obtained from Centre d'Etude du Polymorphisme Humain in France. 1202 was obtained from the National Institute of General Medical Sciences (NIGMS) Human Genetic Cell Repository (Catalog Number 1202B). It is a lymphoblast cell line with 49 chromosomes (XXXXY). CEM and Jurket are T lymphoblastoid cell lines. K562 is a erythroleukemia cell line. CEM and K562 can be obtained from the American Type Culture Collection ("ATCC") under ATCC catalog numbers CCL119 and CCL243, respectively.

The bands detected in the Southern blot are set forth in Table 2 below. For example, the pAC404 insert detected 2 bands of 5.9 and 4.6 kilobase pairs when hybridized with PstI digested K562 cell DNA. The banding pattern obtained for each cell line is unique. Therefore, when used for probe purposes polynucleotide sequences can be characterized, or "fingerprinted" by the banding pattern with known target DNA.

TABLE 2

"Fingerprint" of pAC404

| 7024 | 7351 | CEM | 1202 | Jur. | 7047 | 7432 | 7433 | 7015 | K562 |
|---|---|---|---|---|---|---|---|---|---|
| 6.3 | 6.0 | 6.0 | 4.7 | 4.7 | 5.8 | 6.4 | 4.7 | 6.4 | 5.9 |

TABLE 2-continued

| "Fingerprint" of pAC404 | | | | | | | | | |
|---|---|---|---|---|---|---|---|---|---|
| 7024 | 7351 | CEM | 1202 | Jur. | 7047 | 7432 | 7433 | 7015 | K562 |
| 4.7 | 5.8 | 4.5 | 4.7 | 4.5 | 4.7 | 5.7 | 4.6 | 4.7 | 4.6 | a. The sizes of the fragments are in Kbp.

Example 8—Paternity Testing

Figure 7:
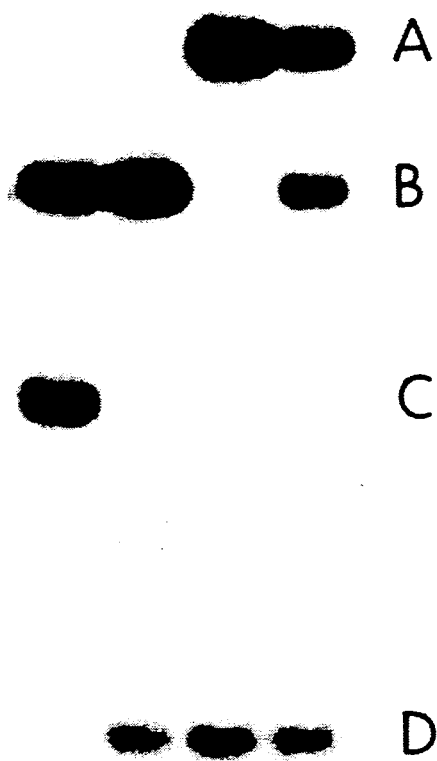
FIG. 7 shows the result of the hybridization blot for a paternity test using pAC404 as a probe.

Genomic DNAs were extracted from a child, the mother of the child, and the alleged father. The DNAs were digested with PstI, electrophoresed, and transferred for Southern Hybridization. The DNA targets were probed with pAC404. FIG. 7 shows the results of the hybridization blot. Lanes 1, 2, and 3 contained DNA from the mother, the child, and the alleged father of the child, respectively. Lane 4 contained a mixture of the child's DNA and the alleged father's DNA. The last lane often helps to resolve ambiguity whenever a band detected in the child's lane is close in size to a band detected in the alleged father's lane. In such a case, the presence of a single band in the relevant size region in the "child plus alleged father" lane would tend to indicate a common allele; and a doublet band would indicate distinct alleles. FIG. 7 shows that Band B in the child was inherited from the mother, but Band D was not inherited from the mother. Since Band D was also present in lane 3, the evidence supports the theory that the alleged father is indeed the biological father.

Example 9—Forensic Testing

Figure 8:
FIG. 8 shows the result of the hybridization blot for a forensic test using pAC404 as a probe.
Figure 8:
Figure 8:
Figure 8:

DNAs were extracted from a rape victim, semen stains found on the victim, and from a suspect of the crime. The DNAs were digested with PstI, and subjected to the Southern hybridization procedure. pAC404 was used as a probe. FIG. 8 shows the results of the hybridization blot. Lane (1) contained DNA from the victim. Lanes (2) and (3) contained DNA from evidence found on the victim, and lane (4) contained DNA from the suspect. The 2 bands (B and C) found in lanes (2) and (3) do not match the bands (A and D) in lane (1), clearly indicating that these bands did not arise from cells of the victim which somehow contaminated the evidence sample. However, both bands (B and C) matched bands of the same sizes in lane 4. Therefore, the results indicate that the DNA from the semen stain came from the suspect.

Example 10—Chromosomal Mapping

The clone pAC404 was mapped to a human chromosome by Southern blot analysis of human - mouse somatic cell hybrids. The presence or absence of fragments detected by the probe pAC404 was determined for 12 Karyotyped hybrids (Table 3). These fragments were always seen when chromosome 18 was present in the hybrid cell line, but were not seen when chromosome 18 was absent. These data clearly assign the fragments detected by pAC404 to chromosome 18.

TABLE 3

| Cell Hybrid | Lila 4 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X |
|---|---|---|---|---|---|---|---|---|---|---|---|---|---|---|---|---|---|---|---|---|---|---|---|---|
| IT-A9 2-21-2 | + | | | | | +a | | + | | | | + | + | | + | | | | + | | + | + | | |
| Call A9 1-9-9 | + | *b | | | | * | | | | | | | + | + | + | | | | + | + | + | + | + | |
| Cal A9 1-13 | + | * | | | | * | | | | | | | + | + | | | | | + | | + | | | |
| A9 Su 1-2 | + | + | * | | | + | | | | | | | + | + | | | * | + | | + | | | | |
| IT A9 1-2 | − | | | | | + | * | * | | | | | | + | | + | + | + | | + | + | | | |
| IT A9 1-13-9 | + | | | | | + | | + | | | | | | + | + | | + | + | | | + | | | |
| IT A9 2-18 | + | | | | | + | * | + | | | | | | | | | + | + | | | + | | | + |
| IT A9 2-21-14 | + | | | | | + | * | * | | | | | | + | | + | + | + | + | | + | | | |
| Anly Rag 1 | + | + | | + | + | + | + | + | * | | * | + | | + | | | + | | | | + | | | * |
| Pj Rag 7-2 | + | + | | + | | + | + | + | + | + | | | + | | + | * | | + | | | | | + | * |
| Rag 194 5-5 | − | | * | + | + | + | + | | | + | | | + | + | + | | + | | | | + | + | + | * |
| 53-87-3 Cl 10 | − | | | | | | | + | | | | | | | | | | | | | | | | | a+: Entire chromosome
b*: Marker chromosome

Deposit of Microorganism

Many polynucleotide sequences may be used to practice the present invention. Exemplary of such sequences are human genomic sequences which have been cloned into recombinant plasmids designated pAC387, pAC388, pAC404, and pAC405. FIG. 4 shows the relationships among the cloned sequences of this invention.

An E. coli strain HB101 carrying the plasmid pAC387, an E. coli strain XL1-BLUE (Stratagene) carrying the plasmid pAC388, an E. coli strain HB101 carrying the plasmid pAC404, and an E. coli strain HB101 carrying the pAC405 plasmid have been deposited with the Agricultural Research Culture Collection (NRRL), Peoria, Ill., on Mar. 22, 1989, and have been assigned accession numbers NRRL B-18468, NRRL B-18469, NRRL B-18470, and NRRL B-18471, respectively.

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the cultures. The depositor acknowledges the duty to replace the deposits should be depository be unable to furnish a sample when requested, due to the condition of the deposits. All restrictions on the availability to the public of the subject culture deposits will be irrevocably removed upon the granting of a patent disclosing them.

E. coli HB101 is available from the NRRL repository where its accession number is NRRL B-11371. Plasmids can be isolated from the E. coli host by use of standard procedures, e.g., using cleared lysate-isopycnic density gradient procedures, and the like.

The present invention is not to be limited in scope by the microorganisms deposited, since the deposited embodiment is intended as a single illustration of one aspect of the invention. Many variations of this invention as herein set forth may be made without departing from the spirit and scope thereof. The specific embodiments described are given by way of example only, and the invention is limited only by the terms of the appended claims.

We claim:
1. A polynucleotide which hybridizes to the human genetic locus D18S27 selected from the group consisting of:
   (a) the human DNA insert in plasmid pAC387;
   (b) the human DNA insert in plasmid pAC388;
   (c) the human DNA insert in plasmid pAC404; and
   (d) the human DNA insert in plasmid pAC405.
2. The polynucleotide, according to claim 1, which is the human DNA insert in plasmid pAC387.
3. The polynucleotide, according to claim 1, which is the human DNA insert in plasmid pAC388.
4. The polynucleotide, according to claim 1, which is the human DNA insert in plasmid pAC404.
5. The polynucleotide, according to claim 1, which is the human DNA insert in plasmid pAC405.
6. A polynucleotide probe which identifies the human gene locus D18S27, wherein said probe comprises an appropriate label and a polynucleotide, wherein said polynucleotide is selected from the group consisting of pAC387, pAC388, pAC404, and pAC405.
7. The polynucleotide according to claim 6, which is pAC387.
8. The polynucleotide probe, according to claim 6, wherein said polynucleotide is pAC388.
9. The polynucleotide probe, according to claim 6, wherein said polynucleotide is pAC404.
10. The polynucleotide probe, according to claim 6, wherein said polynucleotide is pAC405.
11. The polynucleotide probe, according to claim 6, wherein said polynucleotide is pAC387.

* * * * *

UNITED STATES PATENT AND TRADEMARK OFFICE
CERTIFICATE OF CORRECTION

PATENT NO. : 5,192,658
DATED : March 9, 1993
INVENTOR(S) : Zvi Loewy, et al

It is certified that error appears in the above-indentified patent and that said Letters Patent is hereby corrected as shown below:

Column 1, line 18, "Watson-crick" should read --Watson-Crick--.

Column 4, line 37, "Phase Lila 4" should read --Phage Lila 4--.

Column 15, 1 ine 17, "should be depository" should read --should the depository--.

Signed and Sealed this

Thirtieth Day of November, 1993

Attest:

BRUCE LEHMAN

*Attesting Officer*   *Commissioner of Patents and Trademarks*